(12) United States Patent
Mazzarolo

(10) Patent No.: US 8,840,548 B2
(45) Date of Patent: Sep. 23, 2014

(54) USE OF A DATA LOGGER AND A SYSTEM OF SENSORS WHICH DETECT THROUGH A GARMENT INFORMATION RELATING TO PHYSICAL AND/OR BIOMEDICAL PARAMETERS OF A PERSON

(75) Inventor: Giovanni Mazzarolo, Coste di Maser (IT)

(73) Assignee: Alpinestars Research SRL, Treviso (IT)

( * ) Notice: Subject to any disclaimer, the term of this patent is extended or adjusted under 35 U.S.C. 154(b) by 1130 days.

(21) Appl. No.: 11/337,975

(22) Filed: Jan. 23, 2006

(65) Prior Publication Data

US 2006/0155182 A1  Jul. 13, 2006

Related U.S. Application Data

(63) Continuation of application No. PCT/EP2004/006117, filed on Jun. 7, 2004.

(30) Foreign Application Priority Data

Jul. 25, 2003 (IT) .............................. TV2003A0106

(51) Int. Cl.
| | | |
|---|---|---|
| *A61B 5/02* | (2006.01) | |
| *A61B 5/04* | (2006.01) | |
| *A61B 5/00* | (2006.01) | |
| *G01L 1/18* | (2006.01) | |
| *G01L 1/14* | (2006.01) | |
| *A61B 5/11* | (2006.01) | |
| *A41D 13/00* | (2006.01) | |
| *G01L 1/00* | (2006.01) | |
| *A61B 5/01* | (2006.01) | |
| *A61B 5/024* | (2006.01) | |

(52) U.S. Cl.
CPC ................. *A61B 5/6804* (2013.01); *G01L 1/18* (2013.01); *A61B 5/01* (2013.01); *A41D 2600/102* (2013.01); *G01L 1/14* (2013.01); *A41D 2600/104* (2013.01); *A61B 5/0002* (2013.01); *A61B 5/6806* (2013.01); *A41D 13/0015* (2013.01); *A61B 5/02* (2013.01); *A61B 5/024* (2013.01); *A61B 5/11* (2013.01)
USPC ........... 600/301; 600/388; 600/549; 600/552; 600/553; 600/509; 600/500; 600/485; 2/456; 73/862.381

(58) Field of Classification Search
CPC ..................... A41D 13/0015; A41D 2600/102; A41D 2600/104; G01L 1/18–1/186; G01L 1/14–1/148; A61B 5/0002; A61B 5/0024; A61B 5/01; A61B 5/68; A61B 5/6804; A61B 5/6806; A61B 5/11
USPC ......... 600/300–301, 595, 388, 549, 552, 553, 600/509; 702/141; 2/455, 456, 459–467; 73/862.381
See application file for complete search history.

(56) References Cited

U.S. PATENT DOCUMENTS

| | | | | |
|---|---|---|---|---|
| 4,817,633 | A * | 4/1989 | McStravick et al. | 600/595 |
| 4,825,469 | A * | 5/1989 | Kincheloe | 2/456 |
| 5,642,096 | A * | 6/1997 | Leyerer et al. | 340/573.1 |
| 6,032,299 | A * | 3/2000 | Welsh | 2/456 |
| 6,206,837 | B1 | 3/2001 | Brugnoli | |
| 6,783,153 | B2 * | 8/2004 | Mattes | 280/735 |
| 6,836,744 | B1 * | 12/2004 | Asphahani et al. | 702/141 |
| 2001/0024949 | A1 | 9/2001 | Yanagida et al. | |
| 2002/0194934 | A1 * | 12/2002 | Taylor | 73/862.046 |
| 2003/0135127 | A1 | 7/2003 | Sackner et al. | |
| 2003/0140399 | A1 * | 7/2003 | Golde | 2/410 |
| 2003/0182040 | A1 * | 9/2003 | Davidson | 701/45 |
| 2004/0111790 | A1 * | 6/2004 | Dainese | 2/456 |
| 2004/0183283 | A1 * | 9/2004 | Buckman et al. | 280/730.1 |
| 2005/0165284 | A1 * | 7/2005 | Gefen | 600/300 |

FOREIGN PATENT DOCUMENTS

| | | |
|---|---|---|
| DE | 199 27 686 | 3/2001 |
| DE | 19927686 | 3/2001 |
| DE | 100 05 526 | 8/2001 |
| DE | 10005526 | 8/2001 |
| JP | 10500916 | 1/1998 |
| JP | 2001262408 | 9/2001 |
| WO | WO 98/52433 | * 11/1998 |

| WO | 0178577 | 10/2001 |
| WO | 02100200 | 12/2002 |
| WO | WO 02/100200 | 12/2002 |
| WO | WO 2005099497 A1 * | 10/2005 ............ A41D 13/00 |

OTHER PUBLICATIONS

Adams, P. S. et al "Three methods for measuring range of motion while wearing protective clothing: A comparative study"; International Journal of Industrial Ergonomics, 12 (1993) 177-191.*
Liu, T. S. et al; "A Model for a Rider-Motorcycle System Using Fuzzy Control", IEEE Transactions of Systems, Man and Cybernetics, vol. 23, No. 1, Jan./Feb. 1993; p. 267-276.*
NPL_Flexi_Force_Sensors_Manual_2010, p. 1-15.*
International Search Report dated Oct. 15, 2004.
Official Notice of Rejection mailed Jan. 8, 2010 from Japanese Patent Application No. 2006-521402.

* cited by examiner

*Primary Examiner* — William Thomson
*Assistant Examiner* — Marie Archer

(74) *Attorney, Agent, or Firm* — Katten Muchin Rosenman LLP

(57) ABSTRACT

The information relating to physical and/or biomedical parameters of a person carrying out, in real conditions, an activity distinguished by high mechanical stresses is detected by sensors (10, 12, 16, 18, 20, 22, 30) which are mounted on, or form part of, a garment worn while carrying out said activity. During all the stages of said activity this information is converted into data in digital format which are stored in an electronic recording device (100) or "data logger".

Advantages: the stored data may be used by other persons also far from the location where the activity is being performed and/or at a later time.

8 Claims, 3 Drawing Sheets

USE OF A DATA LOGGER AND A SYSTEM OF SENSORS WHICH DETECT THROUGH A GARMENT INFORMATION RELATING TO PHYSICAL AND/OR BIOMEDICAL PARAMETERS OF A PERSON

CROSS-REFERENCE TO RELATED APPLICATION

This application is a continuation of International Application PCT/EP2004/006117 filed on Jun. 7, 2004, now International Publication WO 2005/013816 and claims priority from Italian Application TV2003A000106 filed Jul. 25, 2003, the contents of which are herein wholly incorporated by reference.

DESCRIPTION

The present invention relates to the use of a so-called "data logger" in order to record data relating to the physical and/or biomedical condition of the persons while actually performing an activity distinguished by high mechanical stresses acting on the body, such as for example a high-speed sport.

Data loggers associated with means for detecting exclusively biomedical parameters of persons while exerting physical effort are known, such as that disclosed in the U.S. Pat. No. 6,206,837 where the parameter detected consists in the person's respiration. In order to detect the parameter, however, means are used—in the case in question a mask—which are not compatible with actual carrying out of the activity in real conditions. As a result devices of this kind may only be used in laboratories.

It is also known that manufacturers of garments for motor sports are attempting to provide maximum protection for the end users of their products by proposing solutions able to counteract and/or eliminate the stresses to which the body is subject, for example during car or motorcycle races, in the event of accidents, the consequences of which may also be of a serious nature.

In addition to the development of fireproof and highly resistant materials which constitute so-called "passive protection systems", with the aid of electronic technology it has been possible to design so-called "intelligent garments" or "active protection systems". For example, the patent application WO-A-02 19850 describes a garment comprising a motorcyclist's jacket and a waistcoat or "gilet" containing three inflatable bags which form an air cushion or "air-bag" and also containing a rigid protection for the back. The jacket contains acceleration sensors and the data detected by them are sent to a central control unit so as to trigger, in a dangerous event (falling or impact suffered by the pilot), electrically operated valves which connect three gas cylinders to the said inflatable bags which are normally flat and are concealed inside the jacket. It should be noted that the main purpose of this system is to ensure the automatic activation of the protective system during the dangerous event and that this system does not envisage any recording of the motorcyclist's biomedical data during normal use, i.e. in conditions other than accidents. In the same patent application it is envisaged manufacturing the jacket and the waistcoat using composite textile materials incorporating optical-fibre sensors which convey in real time information in relating to mechanical, physical and thermal parameters to a display which is sewn onto the jacket. This information is for exclusive use of the person wearing the garment and is not recorded. No precise indication is given, however, as to the parameters involved, apart from the relative acceleration of pilot and motorcycle.

Garments equipped with sensors are also known from DE-A-199 27 686 and DE-A-100 05 526 for the purpose is monitoring the health of a patient wearing the garment; from US-A-2001 0024949 for the purpose of detecting a state of emergency which is signaled via a mobile phone upon conversion of the relevant data to speech; WO-A-02 100200 and US-A-2003 0135127 for the purpose of detecting the physical condition of the person wearing the gament which, according to the latter document can also be a person performing an athletic activity.

The main object of the present invention is to provide, also for other persons situated far away and/or at a later time, an information relating to physical and/or biomedical parameters detected directly during carrying out of the abovementioned demanding activities, i.e. in real conditions, by means of at least one of the garments worn by a person. Said detection is performed not only during a dangerous event (falling, impact, etc), but also for the whole of the time said activities are being performed.

This object, together with others, is achieved using a data logger in accordance with the characteristic features claimed hereinbelow.

The particular features of said use and the advantages arising therefrom will emerge more clearly from the following description provided purely by way of a non-limiting example where the activity in which the person is engaged is a motorcycling competition and the garment worn is a bodysuit. In the description reference will be made to the accompanying drawings in which.

Figure 1:
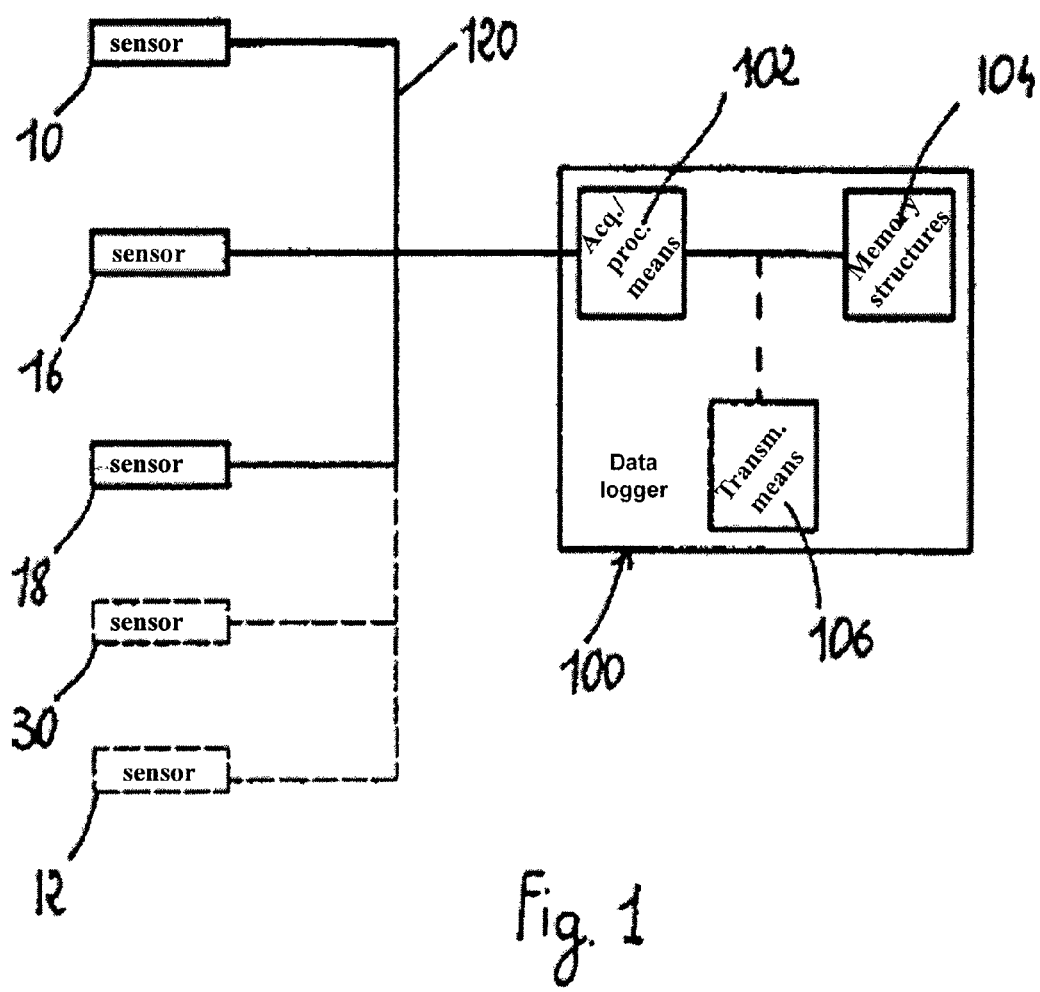
FIG. 1 shows a block diagram of a system for recording physical and/or biomedical data relating to a person during motorcycle racing.

In a motorcycling competition the pilot assumes various riding positions, depending on a series of variables such as the speed, acceleration, riding posture, the characteristics of the circuit, etc. For each riding position every part of the pilot's body is subject to various forces. These forces are of two types: those which through the bodysuit transfer the movement to the pilot's body and those exerted on the bodysuit, and therefore on the body itself, by the fluid within which the pilot is moving, in this case air. The bodysuit 1 is a garment a structure and being of the type intended to protect the body, i.e., physical protection 5 or protective structure 5, when the wearing person is engaged in a sport activity at high speed.

According to the invention, the bodysuit 1 comprises a data logger 100 housed in a position which is usually protected, such as the aerodynamic hump 130 of the bodysuit. Said data logger:

is connected by means of connections 120 to a plurality of sensors 10, 12, 16, 18, 20, 22, 30 which are variable in number and situated in various parts of the bodysuit,;

comprises means 102 for acquiring and processing the information supplied by said sensors;

comprises memory structures 104 for recording the data relating to the parameters detected by said sensors and preferably also for storing permanent data;

may comprise means 106 for remote transmission of the data.

Figure 2:
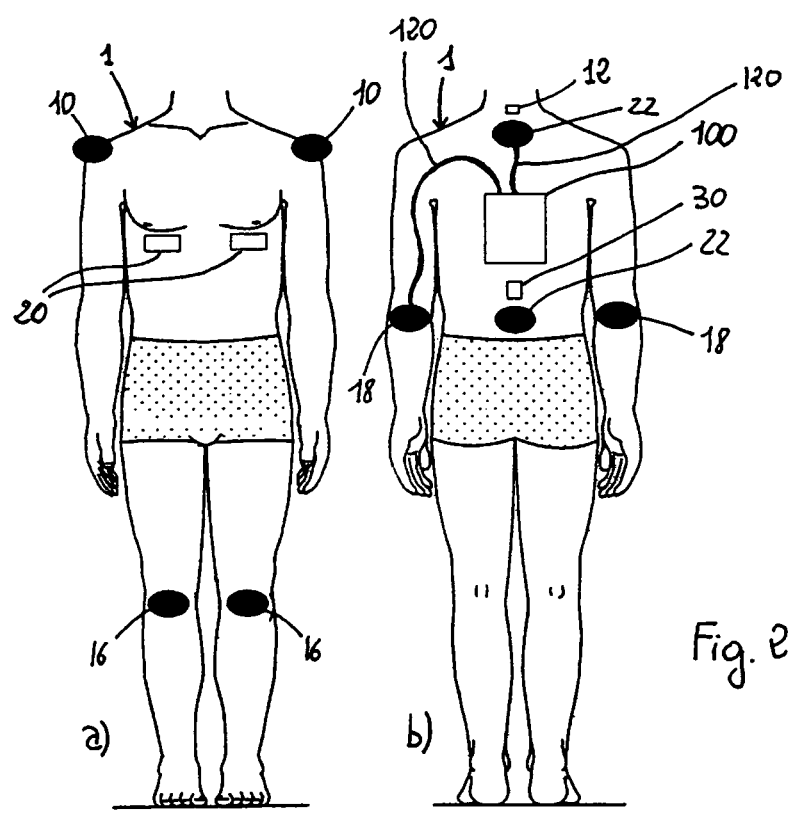
FIGS. 2a and 2b show the position of the various sensors which form part of the system, with respect to the person's body, viewed from the front and rear, respectively.
Figure 3A:
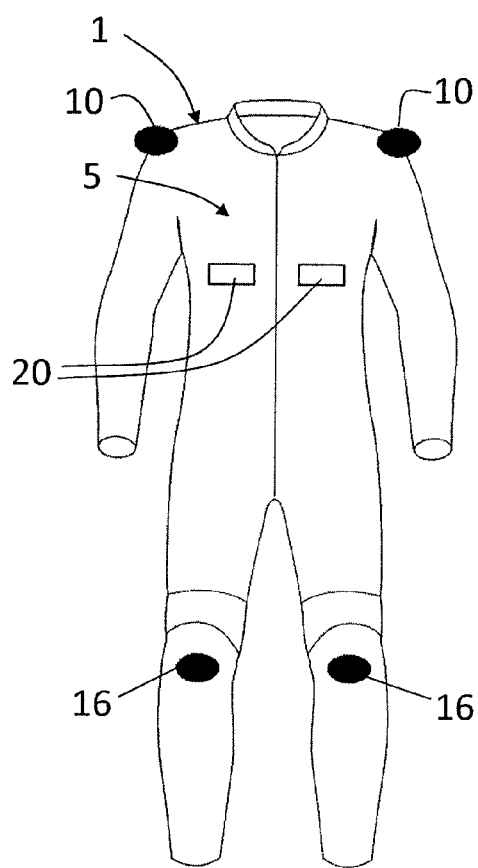
FIGS. 3a and 3b show the position of the various sensors which form part of the system, with respect to a bodysuit, viewed from the front and rear, respectively.
Figure 3B:
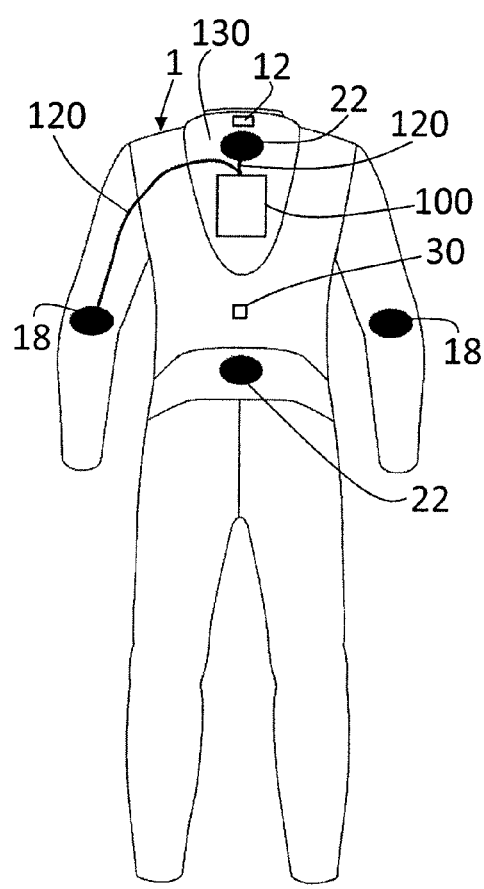

An arrangement of the system according to FIG. 1 is shown in FIGS. 2a and 2b, but in reality the sensors are incorporated in the bodysuit, even though they may be in direct contact with the body of the person.

Said bodysuit, in the region of the shoulders, knees, elbows and ends of the spinal cord, is provided respectively with sensors 10, 16, 18, 22 for detecting the pressure which is exerted by the bodysuit on the person's body, said pressure being positive or negative depending on the direction of the force from which it is derived. Said sensors, for example, may be chosen from among the models "FlexiForce" manufactured by the firm Tekscan. An alternative solution envisages providing, not a single sensor, but an array of smaller sensors. It is thus possible to increase the surface area to be monitored and at the same time obtain within the data a greater definition for the surface area in question.

Said bodysuit also comprises a temperature sensor 30 which is situated in the centre of the back, in the lumbar region, an accelerometer 12 situated below the neck and two plates 20 for sensing the heart rate. It is obvious that the position, the type and the number of all the sensors may vary depending on the application.

Moreover, also depending on the their constructional characteristics and the type of material from which the bodysuit is made (leather, elasticized fabric, meshed fabric, etc.), the sensors may be incorporated into the structure of the bodysuit or may be mounted on the surface in physical contact with the body of the person and/or on the opposite (external) surface.

The data logger 100 is arranged of the rigid aerodynamic hump 130 of the racing bodysuit. Obviously, other locations are possible, such as, for example, mounting the data logger 100, i.e., electronic device 100, on the motorcycle. When it is arranged on the bodysuit, said data logger 100 is connected to the sensors by means of flexible connections 120 which may or may not be incorporated in said bodysuit. Said connections 120 may be of a varying nature, for example leads made of copper, optical fibres, etc., and are chosen in each case depending on the type of signal produced by the sensor (voltage, current, photons, etc.). The conversion of the information into an electrical signal may therefore be performed by means of various systems of transduction (for example from photons to electrical variables or vice versa) and the associated interfaces may be either directly connected to the sensor output or to the input of the data logger 100.

Owing to the possibility of recording and analysing the pressure exerted on the various parts of the pilot's body, and therefore determining the stresses to which the pilot's body is subjected, many applications of the data logger 100 may be envisaged. For example:

in the case of a professional racing team it is possible to assess the riding technique of the pilot and therefore correct any defects associated therewith. This results in an improvement in performances of the person and of the driven vehicle, also providing the possibility of planning an effective race strategy adapted to the circuit;

knowing the stresses it is possible to develop garments which are specifically designed for the individual application. By redefining ad hoc, for example, the structure and the position of the protective systems it is possible to provide the pilot with a garment which is optimized for his/her activity, together with the advantages in terms of safety and reliability, resulting therefrom;

having access to a dynamic recording of the dangerous event as well of its effect on the person's body is of potential interest in the legal sector also; for example, for the purposes of determining civil or criminal responsibility in the case of an accident and preparing evaluations or settling insurance claims;

the data relating to a dangerous event (or in any case all the data, including those detected during an activity without accident) may be processed and transmitted to monitoring operators. In this way immediate transmission of the data concerning a dangerous event to specific operators, for example to medical staff, allows assistance to be provided as rapidly and efficiently as possible. Even if the data are not transmitted to a base station, it is obvious that the rescue personnel, once they have reached the person suffering the accident, are able to obtain information about his/her condition precisely because said information is stored and can be extracted in a comprehensible form from the data logger 100.

It is pointed out that the scope of protection of the present patent, as defined by the claims below, also includes other variations and embodiments. In particular, the garment worn for carrying out an activity may also be different from a bodysuit, namely may be not only a jacket or a pair of trousers, but also a helmet or other garment for protecting the head or a garment for protecting a limb, such as a shoe or a glove.

The invention claimed is:

1. A bodysuit comprising:
a physical protection for a user's body when the user is engaged in a sport activity at a high speed;
a plurality of sensors for measuring parameters affecting the user, the plurality of sensors comprising sensors for determining physical parameters and biomedical parameters of the user;
an electronic device having a memory structure for recording data that are transferred from the plurality of sensors and a processor for processing data that are transferred from the plurality of sensors,
the plurality of sensors comprising a pressure sensor; and
an aerodynamic hump providing a housing, in a position protected against impacts, for said electronic device;
wherein, during all stages of the sport activity, the electronic device detects whether a pressure is exerted by the bodysuit on the user's body due to a movement of the user's body or an external force acting on the bodysuit.

2. The bodysuit according to claim 1, further comprising a connection for transferring of data from the plurality of sensors to the electronic device.

3. The bodysuit according to claim 1, wherein the bodysuit is worn by a person racing a motorcycle or a car.

4. The bodysuit according to claim 1, wherein the bodysuit protects the limbs of the person.

5. A bodysuit for detecting biomedical and physical parameters of a wearer while engaged in a sports activity, the bodysuit comprising:
a protective structure for protecting the wearer during the sports activity;
a physical parameter sensor for detecting a physical parameter to which the wearer is subject;
a biomedical parameter sensor for detecting a biomedical parameter of the wearer;
an electronic device comprising a memory structure for recording data that are transferred from each sensor and a processor for processing data that are transferred from each sensor; and
an aerodynamic hump that provides a housing, in a position protected against impacts, for said electronic device;
wherein the physical parameter sensor comprises a pressure detecting sensor for detecting the pressure exerted by the bodysuit on the wearer's body during all stages of execution of said sports activity, wherein, during all stages of the sports activity, the electronic device detects whether a pressure is exerted by the bodysuit on the user's body due to a movement of the user's body or an external force acting on the bodysuit.

6. The bodysuit of claim 5, further comprising a connection for connecting each sensor to the electronic device.

7. The bodysuit of claim 5, wherein the protective structure comprises one of a motorcycle and automobile racing garment.

8. The bodysuit of claim 5, wherein the protective structure protects a limb of the wearer.

\* \* \* \* \*